United States Patent
Chiprich et al.

(10) Patent No.: US 12,263,251 B2
(45) Date of Patent: Apr. 1, 2025

(54) ORALLY AVAILABLE ARTICLES CONTAINING AT LEAST ONE STABILIZED SUPPLEMENT THEREIN

(71) Applicant: Captek Softgel International, Cerritos, CA (US)

(72) Inventors: Timothy Brian Chiprich, Huntington Beach, CA (US); Argelia Sinay Melendez, Montebello, CA (US); Bibu Philip George, Norwalk, CA (US); David Wood, Yorba Linda, CA (US); Jangsoon Park, Cypress, CA (US); Jung Ku Cho, La Palma, CA (US); Lilyan Hong Tran, Fountain Valley, CA (US); Paul Hwang, Fullerton, CA (US); Ronnie Bayless, Cerritos, CA (US)

(73) Assignee: Captek Softgel International, Cerritos, CA (US)

( * ) Notice: Subject to any disclaimer, the term of this patent is extended or adjusted under 35 U.S.C. 154(b) by 0 days.

(21) Appl. No.: 18/400,346

(22) Filed: Dec. 29, 2023

(65) Prior Publication Data
US 2024/0130977 A1 Apr. 25, 2024

Related U.S. Application Data

(62) Division of application No. 16/141,070, filed on Sep. 25, 2018, now Pat. No. 11,896,720.

(60) Provisional application No. 62/563,562, filed on Sep. 26, 2017.

(51) Int. Cl.
| | | |
|---|---|---|
| A61K 9/50 | (2006.01) |
| A23G 1/00 | (2006.01) |
| A23K 10/18 | (2016.01) |
| A23K 20/10 | (2016.01) |
| A23K 20/174 | (2016.01) |
| A23K 50/20 | (2016.01) |
| A23K 50/30 | (2016.01) |
| A23K 50/40 | (2016.01) |
| A23K 50/50 | (2016.01) |
| A23K 50/70 | (2016.01) |
| A23L 29/206 | (2016.01) |
| A23L 33/105 | (2016.01) |
| A23L 33/135 | (2016.01) |
| A23P 10/30 | (2016.01) |
| A61K 9/00 | (2006.01) |
| A61K 9/48 | (2006.01) |
| A61K 31/715 | (2006.01) |
| A61K 47/36 | (2006.01) |

(52) U.S. Cl.
CPC .............. *A61K 9/5057* (2013.01); *A23G 1/00* (2013.01); *A23K 10/18* (2016.05); *A23K 20/10* (2016.05); *A23K 20/174* (2016.05); *A23K 50/20* (2016.05); *A23K 50/30* (2016.05); *A23K 50/40* (2016.05); *A23K 50/50* (2016.05); *A23K 50/70* (2016.05); *A23L 33/105* (2016.08); *A23L 33/135* (2016.08); *A23P 10/30* (2016.08); *A61K 9/0056* (2013.01); *A61K 9/4808* (2013.01); *A61K 9/4833* (2013.01); *A61K 9/4858* (2013.01); *A61K 9/4891* (2013.01); *A23L 29/206* (2016.08); *A61K 31/715* (2013.01); *A61K 47/36* (2013.01)

(58) Field of Classification Search
CPC ....................................... A23G 1/00
See application file for complete search history.

*Primary Examiner* — Audrea B Coniglio
(74) *Attorney, Agent, or Firm* — FisherBroyles, LLP; Susan M. Oiler

(57) ABSTRACT

Methods of making orally available softgels includes pre-wetting a probiotic with an edible oil to produce a wetted supplement, wherein the edible oil is present in a range of 25% to 75% by weight of a total weight of the probiotic and edible oil, heating the wetted supplement to a temperature in a range of 35° C. to 40° C., blending the wetted supplement and a molten chocolate component together to produce a liquid fill material, encapsulating the liquid fill material in a softgel coating to produce an orally available softgel, and cooling the orally available softgel to have a softgel capsule shell comprising 5% to 15% by weight water. The fill material is a solid at room temperature in the cooled orally available softgel.

15 Claims, No Drawings

US 12,263,251 B2

ORALLY AVAILABLE ARTICLES CONTAINING AT LEAST ONE STABILIZED SUPPLEMENT THEREIN

CROSS-REFERENCE TO RELATED APPLICATIONS

The present application is a divisional of U.S. application Ser. No. 16/141,070, filed Sep. 25, 2018, which claims the benefit of priority of U.S. Provisional Application No. 62/563,562, filed Sep. 26, 2017, which is hereby incorporated by reference in its entirety.

TECHNICAL FIELD

The present disclosure relates to orally available stabilized supplement-containing articles (e.g., softgels). In certain aspects, the stabilized supplement is a probiotic. In some aspects, the stabilized supplement contains a stabilizing component derived from chocolate. In certain aspects, the present disclosure relates to methods of making such stabilized articles.

BACKGROUND

The information provided herein and references cited are provided solely to assist the understanding of the reader, and does not constitute an admission that any of the references or information is prior art to the present invention.

Capsule dosage forms include soft capsules and hard capsules. Capsules are widely used in the pharmaceutical industry as an oral dosage form for the administration of many different types of active pharmaceuticals, vitamin products, and nutritional supplements. The capsules are often filled with an active ingredient in the form of a liquid, a powder, or a powder suspended in liquid.

Hard capsules are often made of unplasticized or low-plasticized gelatin and water to form a stiff capsule that is typically filled with either powder or liquid.

Soft capsules are often made of highly plasticized soft elastic gelatin and often contain a liquid, suspended powder in a liquid, or semisolid ingredients. These capsules are often referred to as "softgel" capsules. Soft capsules can either have a seam or be seamless. Seamed soft capsules can be made using a rotary die encapsulation machine; seamless soft capsules can be made by either coacervation or by the "drop method" using concentric nozzles (i.e, a coextrusion process without mechanical shaping). Soft capsule shells can be made from animal gelatin plasticized with polyhydric alcohols (e.g., glycerol, sorbitol, maltitol, etc.) or from one or more vegetarian capsule-forming materials such as starches, modified starches, carrageenan and alginates or similar polymers, with or without polyhydric alcohol plasticizers.

Soft capsules are now a commonly used dosage form. Soft capsules can provide distinct advantages over more traditional dosage forms such as tablets, hard-shell capsules, and liquids. These advantages include patient compliance and consumer preference, improved bioavailability, speed of product development in many cases, shortened manufacturing time, enhanced drug stability due to less exposure of the active ingredient to oxygen, dose uniformity, and product differentiation, for example through novel shapes.

There are, however, some disadvantages to soft capsules, including the need for specialized manufacturing equipment and the resulting higher cost of manufacturing. Soft capsules are also often problematic because they can become overly soft and clump together excessively and/or become brittle and crack if exposed to temperature and humidity conditions outside of a very narrow range. Difficulties also are encountered when powders are suspended in liquid fill materials due to the powders becoming trapped in the seams of the capsule during encapsulation unless the powders have a very small in particle size.

There are additional difficulties encountered with soft capsules when moisture sensitive ingredients are included in the fill material. For example, if non-spore form probiotic ingredients (e.g., the *acidophilus* and *Bifidobacterium* types of freeze dried probiotic raw materials) are encapsulated in soft capsules, the moisture inherent in the capsule shell rapidly causes a loss in viable colony forming units of the probiotic. Soft capsule manufacturers have gone through elaborate processes in attempts to produce stable probiotic soft capsules due to a demand for easy to swallow soft capsules containing probiotics.

For example, in U.S. Pat. No. 9,427,012 B2, the inventors use elaborate microencapsulation of the probiotic ingredients in an attempt to stabilize them from the deleterious effects of moisture in the capsule shell. Another example is patent application WO2016038355 A1 where the inventors go through elaborate measures in efforts to reduce the water activity of the soft capsule shell, with the goal of enhancing the survival of the non-spore form probiotic bacteria raw materials encapsulated in the fill material.

Both methods described above are prohibitively expensive and not practical in practice. The microencapsulated probiotics described in the '012 patent are more expensive to produce than non-microencapsulated probiotics. In addition, the microencapsulation coatings may be susceptible to interaction with common capsule ingredients and also may encounter physical damage going through the encapsulation machinery. The microencapsulation coating makes the powdered raw materials inherently larger in particle size and make them more difficult to encapsulate without becoming trapped in the seams of the capsules, and causing leaking to occur.

The low water activity soft gelatin capsules described in the '355 patent application are impractical because they rely on a special low melting point gelatin that would likely make the soft capsules overly temperature sensitive. In addition, they are dried to an very low moisture content and are packaged in a special low humidity desiccant bottle that could cause the capsules to become excessively hard and brittle. Such a hard and brittle capsule would likely be prone to damage during shipping and handling.

Accordingly, there is a need for improved soft capsules and methods for their manufacture.

SUMMARY

In accordance with the present invention, there are provided stabilized supplement-containing articles (e.g., softgels). In certain aspects, the stabilized supplement is a probiotic. In certain aspects, the present disclosure provides methods of making stabilized articles (e.g., softgels). In certain aspects, the present disclosure provides methods for the oral delivery of stabilized supplements.

In one aspect, orally available softgel capsules containing at least one stabilized supplement are disclosed herein. In some examples, the softgel comprises a core comprising a supplement, one or more stabilizing components derived from chocolate, and an edible oil, and a capsule shell surrounding the core. In some examples, the softgel is administered as a chewable gel, a swallow-able capsule, a sublingual formulation, or a buccal formulation. In some examples, the one or more stabilizing components derived from chocolate comprise one or more of cocoa solid(s), cocoa butter, and/or cocoa nib paste. In some examples, the edible oil is selected from coconut oil, palm oil, jojoba oil, avocado oil or any other edible oil that has melting point less than 35° C. In some examples, the stabilized supplement is a single strain probiotic, a double strain probiotic, a triple strain probiotic, CoQ10, fish oil, krill oil, vegetable oils containing nutritionally valuable omega fatty acids, water-soluble vitamin, oil-soluble vitamin, mineral, herb, herbal extract, or a combination of any two or more thereof. In some examples, articles comprise an orally available softgel and a protective package. In some examples, the protective package includes a relative humidity controlling salt blend therein to retain desired chew-ability characteristics. In some examples, the protective package prevents the article from reaching a temperature in excess of about 40° C.

In another aspect, methods of making an orally available article containing at least one stabilized supplement therein are described herein. In some examples, the method comprise pre-wetting a powdered supplement with an edible oil to produce a wetted supplement, blending the wetted supplement with a sufficient amount of one or more stabilizing components derived from chocolate to produce a stabilized supplement, and encapsulating the stabilized supplement in a softgel coating to produce the orally available article. In some examples, the stabilized supplement is a solid at room temperature. In some examples, the stabilized supplement has a melting point less than about 40° C. In some examples, the powdered supplement is a non-spore-forming probiotic powder, and in some cases, the non-spore-forming probiotic powder is freeze-dried. In some examples, the non-spore-forming probiotic powder is *Lactobacillus acidophilus* powder and/or *Bifidobacterium lactis* powder. In some cases, the non-spore-forming probiotic powder has at least about 200 Billion Colony Forming Units per gram. In some examples, the powdered supplement comprises one or more of a single strain probiotic, a double strain probiotic, a triple strain probiotic, CoQ10, fish oil, mineral, oil-soluble vitamin or a water-soluble vitamin. In some examples, the orally available article further comprises at least one optional supplement. In some examples, the at least one optional supplement(s) is stabilized. In some cases, the chocolate is dark chocolate. In some cases, the oil used for prewetting constitutes at about 25 to about 75 percent by weight of the wetted supplement.

A patient or subject to be treated by any of the compositions or methods of the present disclosure can mean either a human or a non-human animal. In an embodiment, the present disclosure provides methods for the treatment of a disease or condition in a human patient in need thereof. In another embodiment, the present disclosure provides methods for the treatment of a disease or condition in a veterinary patient in need thereof, including, but not limited to dogs, horses, cats, rabbits, gerbils, hamsters, rodents, birds, aquatic mammals, cattle, pigs, camelids, and other zoological animals.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition (e.g., arresting its development and/or relieving one or more symptoms of the disease, disorder, or condition), causing regression of the disease, disorder, or condition, and/or at least partially alleviating the symptoms of the disease, disorder, or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Accordingly, in some aspects and embodiments of the present disclosure, there are provided methods of treating or preventing a disease or condition, that includes locally administering a formulation of any of the aspects or embodiments as disclosed herein.

DETAILED DESCRIPTION

In accordance with one aspect of the present invention, orally available softgel capsules containing at least one stabilized supplement are disclosed herein. In some examples, the softgel comprises a core comprising a supplement, one or more stabilizing components derived from chocolate, and an edible oil, and a capsule shell surrounding the coreCapsule shells contemplated herein include a softgel shell, a 2-piece hard shell and/or liquid-filled gummies. In certain aspects capsule shells contemplated herein comprise a softgel shell.

Orally available articles (e.g., softgels) contemplated for use herein include articles which can be administered as a chewable gel, a swallow-able capsule, a sublingual formulation, a buccal formulation, a suppository, or a vaginal delivery formulation.

Orally available articles (e.g., softgels) contemplated for use herein include gelatin and vegetarian softgels made on a rotary die Softgel machine, and seamless softgels (see, for example, U.S. Pat. No. 5,478,850 B1, the entire contents thereof is hereby incorporated by reference), and the like.

Orally available articles (e.g., softgels) contemplated for use herein include one or more stabilizing components derived from chocolate, and comprise one or more of chocolate, chocolate liquor, milk chocolate, white chocolate, dark chocolate, cocoa butter, cocoa nib paste, cocoa, cocoa flavonols and the like.

Chocolate is a typically sweet, usually brown food preparation of *Theobroma cacao* seeds, roasted and ground. It is made in the form of a liquid, paste, or in a block, or used as a flavoring ingredient in other foods.

*cacao* has been cultivated by many cultures for at least three millennia in Mesoamerica. The seeds of the *cacao* tree have an intense bitter taste and must be fermented to develop the flavor. After fermentation, the beans are dried, cleaned, and roasted. The shell is removed to produce *cacao* nibs, which are then ground to cocoa mass, an unadulterated chocolate in rough form. Once the cocoa mass is liquefied by heating, it is called chocolate liquor. The liquor also may be cooled and processed into its two components: cocoa solids and cocoa butter.

Baking chocolate, also called bitter chocolate, contains cocoa solids and cocoa butter in varying proportions, without any added sugars. Much of the chocolate consumed today is in the form of sweet chocolate, a combination of cocoa solids, cocoa butter or added vegetable oils, and sugar. Milk chocolate is sweet chocolate that additionally contains milk powder or condensed milk. White chocolate contains cocoa butter, sugar, and milk, but no cocoa solids.

Cocoa solids are a source of flavonoids and alkaloids, such as theobromine, phenethylamine and caffeine. Chocolate also contains anandamide.

Orally available articles (e.g., softgels) contemplated for use herein include edible oils such as coconut oil, palm oil, jojoba oil, avocado oil, fish oil, flaxseed oil, borage oil, soybean oil, sunflower oil, canola oil, medium chain triglycerides oil, olive oil, krill oil, algal oil or any other edible vegetable or animal derived oil.

Orally available articles (e.g., softgels) contemplated herein are useful with a variety of stabilized supplement and/or treating agents, such as, for example, single strain probiotics (either spore form or non-spore form), double strain probiotics, multi strain probiotics, CoQ10, fish oil, krill oil, vegetable oils containing Omega fatty acids (Omega 3, Omega 6, Omega 7, Omega 9 or combinations thereof), water-soluble vitamins, oil-soluble vitamins, minerals, herbs, herbal extracts, isolated herbal phytochemicals, glandular raw materials, enzymes, fiber ingredients, prebiotics, immunosuppressants, anticoagulants, antidepressants, antineoplastic agents, cardiovascular agents, antibiotics, anti-inflammatory agents, and the like, as well as mixtures of any two or more thereof.

Orally available articles (e.g., softgels) contemplated for use herein include liquid fill encapsulated in a soft capsule shell. The soft capsule shell is formed from a material or blends of materials suitable for encapsulating the liquid fill. The material is present in the capsule shell in an amount to yield a soft capsule shell sufficient to encapsulate and protect the liquid fill.

The material (or blend of materials) is typically present in the capsule shell in an amount of at least about 20% by weight; in some embodiments, the material (or blend of materials) is typically present in the capsule shell in an amount of at least about 25% by weight; in some embodiments, the material (or blend of materials) is typically present in the capsule shell in an amount of at least about 30% by weight of the shell. In some embodiments, the material (or blend of materials) is typically present in the capsule shell in an amount of at most about 85% by weight; in some embodiments, the material (or blend of materials) is typically present in the capsule shell in an amount of at most about 70%; in some embodiments, the material (or blend of materials) is typically present in the capsule shell in an amount of at most about 65%; in some embodiments, the material (or blend of materials) is typically present in the capsule shell in an amount of at most about 60% by weight of the capsule shell.

Suitable materials for encapsulating the liquid fill include capsule forming polymers and gelatin. Examples of capsule forming polymers include modified starches, cellulosic polymers, carrageenans, alginates or other natural polymers, and the like.

Preferably, the material is starch or a blend of starch and carrageenan. The gelatin can be natural starch, modified starch, or combinations of any two or more thereof. The starch can be combined with carrageenan which can be iota carrageenan, kappa carrageenan, kappa 2 carrageenan, processed Eucheuma seaweed, and the like, as well as combinations of any two or more thereof.

Natural starch is a polysaccharide made of predominantly amylose and amylopectin that functions as a carbohydrate store in many plants that are used in the human diet. The natural starch can be from any source. Typically, the natural starch is obtained from a vegetarian source. For example, starch can be obtained from tapioca, corn, rice, arrowroot, potato, oats, sorghum, wheat, millet, wheat, rye, barley, buckwheat, beans, peas, lentils, peanut, banana, or other plants.

Modified starches include starch that has been chemically modified by the addition of one or more chemical moeities or that has been physically modified. Physical modification includes pregelatinizing the starch by means of heat; chemical modification can involve any chemical group known to those skilled in the art for chemically modifying starch. For example, appropriate chemical modifications include, alkylation, acylation, hydroxypropylation, phosphatidation, oxidation, acetalization, and the like, as well as combinations of any two or more thereof.

The material which forms the capsule shell typically further includes water. Water is present in the original material mass before the capsules are made, in an amount sufficient to allow the processing of the material on the encapsulation machine. After the capsules are formed the majority of the moisture is removed during the drying process.

To yield a capsule shell having the softness and flexibility in accordance with the present invention, water is typically present in the processed shell at a minimum amount of about 5% by weight; in some embodiments, water is typically present in the shell at a minimum amount of about 6%; in some embodiments, water is typically present in the shell at a minimum amount of about 7% by weight. The maximum amount of water present in the shell is about 15% by weight; in some embodiments, the maximum amount of water present in the shell is about 12% by weight; in some embodiments, the maximum amount of water present in the shell is about 10% by weight, based on the total weight of the processed capsule shell.

The water typically has a plasticizing effect on the material. However, water is generally too volatile to be relied on as the sole plasticizer. Therefore, a non-volatile plasticizer or blend of plasticizers can be added to the material which forms the capsule shell.

The non-volatile plasticizer can be any plasticizer compatible with the material of the capsule shell. For example, the non-volatile plasticizer can be glycerine, maltitol, sorbitan, sorbitol or similar low molecular weight polyhydric alcohols, and the like, as well as mixtures of any two or more thereof. The ratio of plasticizer to material typically determines how hard or soft the shell will be.

The ratio of plasticizer to material in the shell is in an amount sufficient such that the capsules are not too hard, such that the capsules are brittle and crack if stressed during shipping and handling, and are not too soft, such that the capsules become deformed during shipping and handling. Generally, the non-volatile plasticizer is preferably present in the capsule shell from about 8% to 65% by total weight of the capsule shell, most preferably from about 15% to 40% by total weight of the capsule shell.

The material which forms the capsule shell can further contain extenders and/or plasticizers. The plasticizer can be any of those plasticizer described herein.

The extender can be any extender which is compatible with the material. Examples of extenders include natural or modified natural biopolymers and synthetic polymers. Natural biopolymers include, for instance, cellulose, starch, starch derivatives, bacterial polysaccharides such as xanthan gum and gellan gum and vegetable gums such as guar gum, locust bean gum, gum tragacanth, gum Arabic; and animal derived polymers such as chondroitin sulfate, hyaluronic acid, heparin, collagen and chitosan. An example of a modified natural biopolymer is modified cellulose.

Examples of synthetic polymers include carbon chain polymers of the vinyl and acrylic types as well as heterochains of the polyoxide and polyamine types.

The material which forms the capsule shell can also include any acceptable excipient. The excipient can be any excipient compatible with the material. The excipient useful with the material of the capsule shell includes those excipients described above, as well as other excipients such as colorants, sweeteners, flavorings and essential oils, as described herein, to impart an appealing color, taste and/or odor to the coated capsule.

The flavor can be a natural or artificial flavor and typically also is pleasantly fragrant. An example of an edible pleasantly fragrant flavor is vanilla. Other edible fragrant flavors include, but are not limited to, essential oils such as peppermint or rosemary oils.

The sweetener can be a natural or artificial sweetener. An example of a sweetener is *Stevia* extract. Other edible sweeteners include, but are not limited to, sucralose, sucrose, fructose, glucose, xylitol, aspartame, neotame, acesulfame K, glycine, and Luo Han Guo extract.

The colorants can be natural or artificial colorants. An example of a colorant is caramel. Other edible colorants include, but are not limited to, annatto, turmeric, iron oxide, titanium dioxide, FD&C colors, fruit extracts, chlorophyllin, cocoa, and carob extracts.

In accordance with another aspect of the present invention, there are provided articles comprising an orally available article (e.g., softgel) as described herein, and a protective package therefor.

The orally available articles contemplated herein include orally available articles in a protective package, where the protective package includes a relative humidity controlling salt blend therein.

In some embodiments, the protective packages of invention articles prevent the article from reaching a temperature in excess of about 40° C.

In accordance with still another aspect of the present invention, there are provided methods of making an article (e.g., softgel) containing at least one stabilized supplement therein, the method comprising:
  (a) pre-wetting the entire amount of the probiotic powder with an approximately 1:1 ratio of a warmed edible oil held at approximately 35° C. (e.g., in a water bath). This is done so the probiotic powder can be wetted and warmed to the same temperature at which the rest of the fill material (which melts between 35 and 40° C.) will be maintained. This prewetting/warming step serves to prevent solidification and content uniformity problems that may otherwise occur if the room temperature probiotic powder was added directly to the molten fill material. If needed, one or more stabilizing components derived from chocolate may also be included in order that the weight of the edible oil plus chocolate component is equal to the weight of the probiotic powder. The edible oil (and chocolate component if needed to reach the desired amount) is warmed to a temperature that will allow it to be mixed with the remainder of the fill material in a molten state that is at the same temperature so as to prevent both overheating the probiotic and to prevent content uniformity problems.
  (b) blending the pre-wetted warmed probiotic powder with a sufficient amount of one or more molten stabilizing components derived from chocolate held at approximately 35° C. to produce a stabilized supplement; and
  (c) encapsulating the stabilized supplement in a softgel.

In some examples, methods of making an orally available article containing at least one stabilized supplement include:
  (a) pre-wetting a powdered supplement with an edible oil to produce a wetted supplement,
  (b) blending the wetted supplement with a sufficient amount of one or more stabilizing components derived from chocolate to produce a stabilized supplement, and
  (c) encapsulating the stabilized supplement in a softgel coating to produce the orally available article.

In some aspects of the methods described herein, non-spore-forming probiotic powder is freeze-dried.

In some aspects of invention methods, the amount of edible oil used is sufficient to reduce the melting point of the one or more stabilizing components derived from chocolate below about 40° C. In some examples, the oil that is mixed with the powered supplement to produce a wetted supplement constitutes at about 25 to about 75 percent by weight of the wetted supplement. In other cases, the oil is present at about 30 to about 70 percent, about 35 to about 65 percent, about 40 to about 60 percent, about 45 to about 55 percent by weight of the wetted supplement. In other examples, the ratio of oil to powdered supplement is about 1:3, about 1:2, about 1:1, about 1:2, or about 1:3 by weight.

In some aspects, the supplement employed in the invention methods is a single strain probiotics (either spore form or non-spore form), double strain probiotics, multi strain probiotics, CoQ10, fish oil, krill oil, vegetable oils containing Omega fatty acids (Omega 3, Omega 6, Omega 7, Omega 9 or combinations thereof), water-soluble vitamins, oil-soluble vitamins, minerals, herbs, herbal extracts, isolated herbal phytochemicals, glandular raw materials, enzymes, fiber ingredients, prebiotics, immunosuppressants, anticoagulants, antidepressants, antineoplastic agents, cardiovascular agents, antibiotics, anti-inflammatory agents, and the like.

In some cases, the supplement is a non-spore-forming probiotic powder. In some examples, the non-spore-forming probiotic powder has at least about 200 Billion Colony Forming Units per gram. In some examples, he non-spore-forming probiotic powder has at least about 100 Billion Colony Forming Units per gram, at least about 150 Billion Colony Forming Units per gram, at least about 250 Billion Colony Forming Units per gram, or at least about 300 Billion Colony Forming Units per gram In some aspects, additional, optionally stabilized supplement(s) may be included in the invention method. Such additional supplement(s) are optionally stabilized.

In some aspects, invention methods employ dark chocolate (otherwise known as bittersweet chocolate) as the stabilizer. In some embodiments, the chocolate is characterized by being a solid at room temperature but being molten below 40° C., below 39° C., below 38° C., below 37° C., below 36° C., below 35° C., below 34° C., and below 33° C.

As readily recognized by those of skill in the art, any softgel is suitable for use herein, such as, for example, softgel materials described in U.S. Pat. Nos. 5,614,217, 7,807,194, and US Pat. Publication No. US2005/0152969, the contents of each of which is hereby incorporated by reference herein in their entirety.

In accordance with another aspect of the present invention there are provided chewable softgels produced by any of the methods described herein.

In accordance with yet another aspect of the present invention, there are provided methods for delivering an orally available stabilized supplement to a subject in need thereof, the method comprising administering to the subject an orally available article (e.g., softgel) as described herein.

Additional Formulation Ingredients

The formulations contemplated for use herein may also contain other components such as, but not limited to, additives, adjuvants, buffers, sweeteners, flavors, bioadhesive polymers, and preservatives.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the active component thereof, to adjust the osmolality of the composition, to adjust the viscosity of the composition, or for another reason, such as effecting drug delivery. Non-limiting examples of pharmaceutical additives of the present disclosure include sugars, such as, sucrose, fructose, glucose, trehalose, mannose, D-galactose, and lactose. In an embodiment, the sugars may be incorporated the composition prior to adding the desired active ingredients such as the probiotics.

The following examples are provided to further illustrate aspects of the invention. These examples are non-limiting and should not be construed as limiting any aspect of the invention.

Example 1: Preparation of Vegetarian Softgels

Vegetarian softgels according to the present invention were prepared as follows.

The fill material was prepared by mixing the probiotic raw materials into molten chocolate/coconut oil blend at approximately 35° C.

| Ingredient | Label Claim per capsule | mg/ capsule |
|---|---|---|
| Bittersweet Chocolate (Chocolate liquor, sugar, cocoa butter, soy lecithin, vanilla) | Not applicable | 372.6 |
| Coconut Oil | Not applicable | 41.4 |
| *Lactobacillus acidophilus* powder (200 Billion Colony Forming Units/gram) | Not less than 5 Billion CFU | 30.0 |
| *Bifidobacterium lactis* powder (300 Billion Colony Forming Units/gram) | Not less than 5 Billion CFU | 20.0 |
| *Bacillus coagulans* powder (200 Billion Colony Forming Units/gram) | Not less than 5 Billion CFU | 36.0 |

The above fill material was then encapsulated on a rotary die Softgel machine using a vegetarian softgel shell formula consisting of: Purified Water, Modified Starch, Carrageenan, Glycerol, Sorbitol.

The soft capsules produced were then dried under low humidity conditions until the capsule shell contained approximately 10% water. The capsules were then assayed for the number of viable colony forming units per softgel and the results were all well above the label claim of 5 billion colony forming units of each of the probiotic strains.

For comparison, a control soft capsule formula was made using the same quantity of the *Lactobacillus acidophilus* probiotic raw material per capsule, but using a base made of medium chain triglyceride oil, white beeswax and soy lecithin. The resulting combination was also encapsulated, dried and then assayed for the number of viable colony forming units per softgel; the results were well below the label claim of 5 billion colony forming units of each of the probiotic strains.

This test shows that the fill material containing the chocolate showed improved stabilization of the probiotic raw materials.

Example 2: Effect of Exposure of Invention Softgels to Defined Relative Humidity Vegetarian softgels prepared as described in Example 1 were exposed to different relative humidity (RH) conditions in jars containing saturated salt solutions that produce the desired relative humidity; the treated capsules were then chewed to see how the properties thereof varied as a function of RH exposure, specifically what RH made them chewable enough to be easy to chew but not so soft that one would be concerned with the softgels becoming sticky and clumping together or being too rubbery. The exposures tested, and the resulting properties are summarized below:

11% RH exposure resulted in a very brittle, crunchy softgel; although it was still possible to chew it up; this material is probably too hard and brittle for most people to enjoy chewing; in addition, at this RH exposure, the capsules are brittle enough to crack during shipping.

33% RH exposure resulted in softer capsules, but were still a bit crunchy. The capsules break up easily as they are being chewed.

43% RH exposure resulted in soft, easy to chew capsules that are not crunchy; while these capsules are soft, they are not so soft as to raise the concern that such capsules would be soft enough to deform and/or stick together.

58% RH exposure resulted in a soft, rubbery, easy to chew capsule that may be too rubbery for some consumers; in addition, the softness of the resulting capsule would render them to be prone to deform and/or clump together.

Based on the preceding observations, in certain embodiments, the target range for the RH exposure (using the custom made desiccant bottles that contain a blend of salts that produce a fixed RH) would be about 30-45% RH. In other embodiments, the target range for the RH exposure is about 20-60% RH depending on specific requirements (for example, if a customer wants them to be more rubbery or more crunchy).

Packaging exists where relative humidity controlling salt blends are incorporated similar to desiccants either as a cartridge or packet inserted into the bottle or built into a compartment attached to the cap of the bottle. Such a bottle would allow soft capsules contained within the bottle to maintain the chew-ability characteristics described above. The packaging can also be enclosed in an envelope or pouch containing thermal insulating bubble wrap either with or without an insert-able ice pack to maintain a temperature below the melting point of chocolate (approximately 40° C.) so that the products stability can be maintained even during the final mailing of the product to an end consumer.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including", containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A method of making an orally available softgel, the method comprising:
   pre-wetting a probiotic with an edible oil to produce a wetted supplement, wherein the edible oil is present in a range of 25% to 75% by weight of a total weight of the probiotic and edible oil;
   heating the wetted supplement to a temperature in a range of 35° C. to 40° C.;
   blending the wetted supplement and a molten chocolate component together to produce a liquid fill material;
   encapsulating the liquid fill material in a softgel coating to produce an orally available softgel; and
   cooling the orally available softgel to have a softgel capsule shell comprising 5% to 15% by weight water;
   wherein the fill material is a solid at room temperature in the cooled orally available softgel.

2. The method of claim 1, wherein the chocolate component is selected from the group consisting of chocolate liquor, milk chocolate, white chocolate, dark chocolate, cocoa butter, cocoa nib paste, cocoa solid, cocoa flavanol, and combinations thereof.

3. The method of claim 1, wherein the chocolate component is dark chocolate.

4. The method of claim 1, wherein the chocolate component is a balance of the fill material.

5. The method of claim 1, wherein the orally available softgel is a chewable softgel capsule, a swallow-able capsule, a sublingual capsule, or a buccal capsule.

6. The method of claim 1, wherein the concentration of edible oil enables the probiotic to melt below 40° C.

7. The method of claim 1, wherein the edible oil is selected from the group consisting of coconut oil, palm oil, jojoba oil, avocado oil, and combination thereof.

8. The method of claim 1, wherein the edible oil has a melting point less than 35° C.

9. The method of claim 1, wherein the edible oil and the probiotic are present in a ratio of 1:3 to 3:1 oil to probiotic.

10. The method of claim 1, wherein the edible oil and the probiotic are present in a ratio of 1:2 and the stabilizing component and edible oil are present in a ratio of 9:1.

11. The method of claim 1, wherein the probiotic is a non-spore-forming probiotic powder.

12. The method of claim 11, wherein the non-spore-forming probiotic powder is freeze-dried.

13. The method of claim 11, wherein the non-spore-forming probiotic powder is *Lactobacillus acidophilus* powder and/or *Bifidobacterium lactis* powder.

14. The method of claim 11, wherein the non-spore-forming probiotic powder has at least about 200 Billion Colony Forming Units per gram.

15. The method of claim 1, wherein the method comprises:
   adding a secondary supplement to the wetted supplement;
   wherein the second supplement is selected from the group consisting of CoQ10, fish oil, krill oil, a vegetable oil comprising omega 3, omega 6, omega 7, omega 9 fatty acids or combinations thereof, a water-soluble vitamin, an oil-soluble vitamin, a mineral, an herb, an herbal extract, and a combination of any two or more thereof.

* * * * *